(12) United States Patent
Hwang et al.

(10) Patent No.: US 8,653,143 B2
(45) Date of Patent: Feb. 18, 2014

(54) **USE OF PANDURATIN DERIVATIVE OR *BOESENBERGIA PANDURATA* EXTRACT**

(75) Inventors: Jae-Kwan Hwang, Goyang-si (KR); Do Un Kim, Seongnam-si (KR)

(73) Assignees: Newtree Co., Ltd., Sungnam, Gyeonggi-Do (KR); Jae Kwan Hwang, Goyang, Gyeonggi-Do (KR)

( * ) Notice: Subject to any disclaimer, the term of this patent is extended or adjusted under 35 U.S.C. 154(b) by 21 days.

(21) Appl. No.: 13/123,519

(22) PCT Filed: Oct. 9, 2009

(86) PCT No.: PCT/KR2009/005804
§ 371 (c)(1),
(2), (4) Date: Dec. 5, 2011

(87) PCT Pub. No.: WO2010/041908
PCT Pub. Date: Apr. 15, 2010

(65) Prior Publication Data
US 2012/0088840 A1     Apr. 12, 2012

(30) Foreign Application Priority Data
Oct. 9, 2008 (KR) .................. 10-2008-0099367

(51) Int. Cl.
*A61K 31/12* (2006.01)

(52) U.S. Cl.
USPC .......................................... 514/683

(58) Field of Classification Search
USPC .......................................... 514/683
See application file for complete search history.

(56) References Cited

U.S. PATENT DOCUMENTS 7,799,782 B2 *     9/2010     Munson et al. ............ 514/234.5

OTHER PUBLICATIONS

Yoshikawa et al. CAS: 149:327396, 2008.*
Win et al., The Journal of Natural Products, 2007, 70(10): 1582-1587.*
Morikawa et al., Chemical & Pharmaceutical Bulletin,2008, 56(7), 956-962.*

* cited by examiner

*Primary Examiner* — Rei-tsang Shiao
(74) *Attorney, Agent, or Firm* — Edwards Wildman Palmer LLP (57) ABSTRACT

The present invention relates to a novel use of a panduratin derivative or a *Boesenbergia pandurata* extract. More specifically, the invention relates to a composition for preventing and treating/relieving a metabolic disease selected from a group consisting of obesity, hyperlipidemia, hypercholesterolemia and diabetes, containing a panduratin derivative represented by Chemical Formula 1, 2 or 3 or a *Boesenbergia pandurata* extract as an active ingredient, a method for treating a metabolic disease selected from a group consisting of obesity, hyperlipidemia, hypercholesterolemia and diabetes, by administering an effective amount of the panduratin derivative or the *Boesenbergia pandurata* extract to a subject in need thereof, and a use of the panduratin derivative or the *Boesenbergia pandurata* extract to prepare a reagent for preventing and treating/relieving a metabolic disease selected from a group consisting of obesity, hyperlipidemia, hypercholesterolemia and diabetes.

2 Claims, 8 Drawing Sheets

Fig. 5 high-fat diet control group  sibutraimine-administered group  panduratin A group

Fig. 6 high-fat diet control group    sibutraimine-administered group    panduratin A group

Fig. 7 high-fat diet control group    sibutraimine-administered group    panduratin A group

■ Cell: HepG2

Fig. 13

■ Cell: differentiatied L6

Fig. 14

USE OF PANDURATIN DERIVATIVE OR BOESENBERGIA PANDURATA EXTRACT

CROSS-REFERENCE TO RELATED APPLICATIONS

This application is the U.S. national phase, pursuant to 35 U.S.C. §371, of PCT international application Ser. No. PCT/KR2009/005804, filed Oct. 9, 2009, designating the United States and published on Apr. 15, 2010, as publication WO/2010/041908; which claims priority to Korean Application No. 10-2008-0099367, filed Oct. 9, 2008. The entire contents of the aforementioned patent applications are incorporated herein by reference.

TECHNICAL FIELD

This application claims priority to Korean Patent Application No. 10-2008-0099367 filed on Oct. 9, 2008, which is hereby incorporated by reference herein.

The present invention relates to a novel use of a panduratin derivative or a *Boesenbergia pandurata* extract. More specifically, the invention relates to a composition for preventing and treating/relieving a metabolic disease selected from a group consisting of obesity, hyperlipidemia, hypercholesterolemia and diabetes, containing a panduratin derivative represented by Chemical Formula 1, 2 or 3 or a *Boesenbergia pandurata* extract as an active ingredient, a method for treating a metabolic disease selected from a group consisting of obesity, hyperlipidemia, hypercholesterolemia and diabetes, by administering an effective amount of the panduratin derivative or the *Boesenbergia pandurata* extract to a subject in need thereof, and a use of the panduratin derivative or the *Boesenbergia pandurata* extract to prepare a reagent for preventing and treating/relieving a metabolic disease selected from a group consisting of obesity, hyperlipidemia, hypercholesterolemia and diabetes.

BACKGROUND ART

Obesity is a medical condition in which body fat has accumulated overly due to the imbalance between the intake and consumption of energy. Obesity is attributable to many causes, including genetic factors, environmental factors such as westernized diet, psychological factors such as stress, and so forth. But, the exact cause or its mechanism has not been clearly elucidated. In addition to its own risk, obesity increases the likelihood of hyperinsulinemia, arteriosclerosis and cardiovascular diseases. Therefore, many studies are underway globally for the treatment of obesity (*Nature*, 404: 635643, 2000; *JAMA*, 282: 15231529, 1999).

Representative obesity-treating drugs include Reductil™ (Abbott, USA), Xenical™ (Roche, Switzerland) and Exolise™ (Arkopharma, France). However, because of side effects associated with cardiac, respiratory and neurologic disorders as well as short-lasting effect, development of more effective obesity-treating drugs is necessary. The current strategy for development of anti-obesity drugs is focused on reducing appetite, lowering caloric absorption, increasing thermogenesis, regulating energy metabolism, regulating signal transduction via the nervous system, and the like (*Nature*, 404: 635643, 2000). Despite the continued efforts to treat obesity based on these strategies, it is not easy to develop a drug satisfying both the safety and efficiency requirements. In this regard, to find and use the ingredients conforming to the obesity-treating strategy from natural products with well-proven safety will be more efficient than to develop synthetic drugs.

Sterol regulatory element-binding proteins (SREBPs) are important transcription factors that activate the enzymes involved in the biosynthesis of fatty acid and cholesterol and thus regulate the synthesis of cholesterol and fatty acid in the liver and adipocytes. Hyperinsulinemia caused by insulin resistance increases expression of SREBP1 in the liver, resulting in accumulation of triglyceride in the liver and fat tissue (Horton, J. D., et al., *Proc Natl Acad Sci USA*, 95, 5987-5992, 1998). Thus, it is regarded that SREBP1 plays a key role in fatty liver induced by insulin resistance.

5' AMP-activated protein kinase (AMPK) is an enzyme that is mainly expressed in tissues related with energy metabolism, such as the liver, muscles and fats, and plays an important role in cellular energy metabolism. AMPK becomes activated when cellular energy level is decreased due to exercise, hypoxia, ischemia, etc. and thus regulates metabolism-related enzymes. That is to say, by regulating fatty acid and cholesterol synthesis, fatty acid oxidation and glycolysis, it restores the intracellular energy balance. Accordingly, it has attracted a lot of attention as a target gene for development of treatments for various metabolic diseases including diabetes, obesity, or the like.

AMPK inhibits fatty acid synthesis by phosphorylating and inactivating the fatty acid synthase, acetyl-CoA carboxylase (ACC), and stimulates fatty acid oxidation by increasing the activity of carnitine parmitoyltransferase 1 which transports fatty acids into the mitochondria (Winder W W, Hardie D G. *Am J Physiol* 270: E299-304, 1996).

Also, AMPK inhibits cholesterol synthesis by inhibiting the activity of 3-hydroxy-3-methylglutaryl-CoA reductase (HMGR), a key enzyme in cholesterol biosynthesis (Henin, N., M. F. Vincent, H. E. Gruber, and G. Van den Berghe. *FASEB J.* 9: 541-546, 1995).

AMPK is known to facilitate cellular glucose uptake by translocating glucose transporter 4 (GLUT4) to the plasma membrane independently of the insulin signaling. Indeed, the antidiabetic drug metformin reduces blood sugar level by activating AMPK (Kurth-Kraczek E J, Hirshman M F, Goodyear L J, Winder W W. *Diabetes* 48 (8): 166771, 1999; Winder W W. Hardie D G. *Am J Physiol* 270: E299-304, 1996).

DISCLOSURE

Technical Problem

While the inventors of the present invention have carried out researches on finding natural materials having anti-obesity, lipid accumulation inhibiting and anti-diabetes activities and safely applicable, they confirmed that extract of *Boesenbergia pandurata*, a kind of Zingiberaceae family or panduratin derivatives isolated from thereof has excellent effects on weight loss, body fat loss and anti-diabetes thereby completing the present invention.

The object of the present invention is to provide novel use of panduratin derivatives or extract of *Boesenbergia pandurata*.

Technical Solution

To achieve the above object, the present invention provides a composition for preventing and treating a metabolic disease selected from a group consisting of obesity, hyperlipidemia, hypercholesterolemia and diabetes, comprising a panduratin derivative represented by Chemical Formula 1, 2 or 3 as an active ingredient.

To achieve another object, the present invention provides a composition for preventing and treating a metabolic disease selected from a group consisting of obesity, hyperlipidemia, hypercholesterolemia and diabetes, containing a *Boesenbergia pandurata* extract as an active ingredient.

To achieve still another object, the present invention provides a method for treating a metabolic disease selected from a group consisting of obesity, hyperlipidemia, hypercholesterolemia and diabetes by administering to a subject in need thereof an effective amount of a panduratin derivative represented by Chemical Formula 1, 2 or 3 or salts thereof.

To achieve still another object, the present invention provides a use of a panduratin derivative represented by Chemical Formula 1, 2 or 3 or salts thereof to prepare an agent for preventing and treating a metabolic disease selected from a group consisting of obesity, hyperlipidemia, hypercholesterolemia and diabetes.

To achieve still another object, the present invention provides a method for treating a metabolic disease selected from a group consisting of obesity, hyperlipidemia, hypercholesterolemia and diabetes by administering to a subject in need thereof an effective amount of extract of *Boesenbergia pandurata*.

To achieve still another object, the present invention provides a use of extract of *Boesenbergia pandurata* thereof to prepare an agent for preventing and treating a metabolic disease selected from a group consisting of obesity, hyperlipidemia, hypercholesterolemia and diabetes.

Hereafter, the present invention is described in detail.

A composition of the present invention comprises a panduratin derivative represented by Chemical Formula 1, 2 or 3 or extract of *Boesenbergia pandurata* comprising thereof and has excellent effects on preventing and treating obesity, hyperlipidemia, hypercholesterolemia or diabetes.

<Chemical Formula 1>

<Chemical Formula 2>

<Chemical Formula 3>

The panduratin derivatives represented by Chemical Formula 1, 2 and 3 refers panduratin A, isopanduratin A and 4-hydrosypanduratin A respectively and they can be isolated and purified by synthesis or from natural materials by using techniques well known in the art. Preferably, panduratin derivatives of the present invention may be isolated and purified from *Boesenbergia pandurata*.

*Boesenbergia pandurata* is a kind of Zingiberaceae family and it is also called *Kaempferia pandurata*. *Boesenbergia pandurata* comprises pinocembrin chalcone, cardamonin, pinocembrin, pinostribin, 4hydroxypaduratin A, panduratin A and isopanduratin A. The ingredients are known to have anti-cancer activity (Trakoontivakorn, G., et. al., J. Arig. Food Chem., 49, 30463050, 2001; Yun, J. M., et. al., Carcinogenesis, 27(7), 14541464, 2006), anti-inflammatory activity (Yun, J. M., et. al., Planta Medica, 69, 11021108, 2003), anti-skin aging activity (Shim, J. S., et. al., Planta Medica, 74, 239244, 2008) or anti-bacterial activity (Hwang, J. K., et. al., Int. J. Antimicrob. Agents, 23, 377381, 2004; Park, K. M., et. al., Food Sci. Biotechnol., 14(2), 286289, 2005), but nothing is known about anti-obesity activity and activity related to metabolic diseases before the present invention.

A panduratin derivative comprised in a composition of the present invention may be prepared by isolating and purifying rhizome of dry *Boesenbergia pandurata* using distilled water acceptable for food processing, ethanol and subcritical water or supercritical carbon dioxide, or from oil obtained by pressing *Boesenbergia pandurata*. To obtain a panduratin derivative comprised in a composition of the present invention or extract comprising thereof, as a extraction solvent, methanol, propanol, isopropanol, butanol, acetone, ether, benzene, chloroform, ethylacetate, methylenechloride, hexane, cyclohexane, petroliumether may be used alone or in combination as well as above-mentioned solvent.

For the isolation and purification of the panduratin derivative from the *Boesenbergia pandurata* extract, column chromatography or high-performance liquid chromatography (HPLC) using silica gel, activated alumina or various other synthetic resins may be used alone or in combination, although not limited thereto.

As an embodiment of the present invention, the panduratin derivative represented by Chemical Formula 1, 2 and 3 were extracted and isolated from the *Boesenbergia pandurata* extract respectively (See Examples 1 to 4).

In another example, each isolated panduratin derivative was administered to mice in which obesity was induced with a high-fat diet. Although the food intake did not change appreciably, body weight was reduced effectively. Furthermore, total blood cholesterol level, triglyceride level, total lipid level, and leptin level also decreased. In addition, body fat, size of adipocytes, and the subcutaneous fat layer were also decreased (see Examples 5-11).

In another example, it was confirmed that the *Boesenbergia pandurata* extract including the panduratin derivatives also result in reduced body weight and body fat (Examples 12 and 13).

In another example, it was confirmed that the panduratin derivatives of the present invention increase the activity of the metabolic protein AMPK in metabolic cells (liver and muscle cells), reduces the inactivated form of its substrate, i.e. the fat-producing protein ACC, and reduces fat-producing protein transcription factor, suggesting that they are effective for metabolic diseases including obesity and diabetes (Examples 14-16).

Accordingly, the present invention provides a composition for preventing and treating a metabolic disease selected from a group consisting of obesity, hyperlipidemia, hypercholesterolemia and diabetes, comprising a panduratin derivative represented by Chemical Formula 1, 2 or 3 or a *Boesenbergia pandurata* extract as an active ingredient. The composition of the present invention may be a pharmaceutical composition or a food composition.

Further, the present invention provides a method for treating a metabolic disease selected from a group consisting of obesity, hyperlipidemia, hypercholesterolemia and diabetes, by administering an effective amount of a panduratin derivative represented by Chemical Formula 1, 2 or 3 or a *Boesenbergia pandurata* extract to a subject in need thereof. In addition, the present invention provides a use of a panduratin derivative represented by Chemical Formula 1, 2 or 3 or a *Boesenbergia pandurata* extract to prepare a reagent for preventing and treating or a food composition relieving a metabolic disease selected from a group consisting of obesity, hyperlipidemia, hypercholesterolemia and diabetes.

The panduratin derivative of the present invention may be used as it is or in the form of a pharmaceutically acceptable salt. As used herein, the phrase "pharmaceutically acceptable" means that the components present in the composition are physiologically acceptable and usually do not invoke allergic or similar reactions when administered to humans. Specifically, the salt may be an acid addition salt formed from a pharmaceutically acceptable free acid. The free acid may be an organic or inorganic acid. The organic acid includes but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. And, the inorganic acid includes but is not limited to hydrochloric acid, bromic acid, sulfuric acid and phosphoric acid.

A pharmaceutical composition of the present invention may comprise pharmaceutically effective amount of the panduratin derivative or the *Boesenbergia pandurata* extract alone or together with one or more pharmaceutically acceptable carrier additionally. As used herein, "pharmaceutically acceptable amount" refers the mount showing more reaction than negative control and preferably, it refers the sufficient amount to treat or prevent obesity, hyperlipidemia, hypercholesterolemia or diabetes. A pharmaceutical composition of the present invention may comprise 0.01 to 99.99 weight % of the panduratin derivative or the *Boesenbergia pandurata* extract and the rest may be a pharmaceutically acceptable carrier.

The pharmaceutically effective amount of the panduratin derivative or the *Boesenbergia pandurata* extract of the present invention is 0.001 to 100 mg/day/kg body weight and preferably 0.01 to 10 mg/day/kg body weight/day. However, the pharmaceutically effective amount suitably determined by considering various factors, such as disease, severity thereof, age of patient, body weight, health condition, sex, diet administration route and administration time.

As used herein, "pharmaceutically acceptable" means non-toxic composition which is physiologically acceptable and, when administered to human beings, generally does not cause allergic reactions, such as gastrointestinal disorder and dizziness, or similar reactions thereto as well as not inhibiting reaction of an active ingredient. The carrier comprises all kinds of solvents, dispersing media, oil-in-water or water-in-oil emulsions, water soluble compositions, liposomes, microbeads and microsomes.

The pharmaceutical composition of the present invention may be formulated with a proper carrier according to administration routes. The administration routes of the pharmaceutical composition of the present invention comprise, but not limited thereto, oral or parenteral routes. The parenteral routes comprise, for example, subcutaneous, intranasal, peritorial, intramuscular, intracutaneous, or intravenous administration.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise anti-coaglutinating agent, lubricant, wetting agents, flavors, emulsifying agents and antiseptics.

Also, in case of parenteral administration, a pharmaceutical composition of the present invention may be formulated with a proper carrier for parenteral administration into injections, transdermal preparations, and nasal inhalers by using the method known in the art. The injection must be sterilized and protected from microorganisms such as bacteria and fungi. Proper carriers for injection may be, but not limited thereto, water, ethanol, polyol (e.g. glycerol, propylene glycol and liquid polyethylene glycol) or mixture thereof and/or solvent or dispersing media comprising plant oil. More preferably, proper carriers may be Hank's solution, Ringer's solution, PBS (Phosphate buffered saline) containing triethanol amine, or a isotonic solution such as distilled water for injection, 10% ethanol, 40% ethanol, 40% propylene glycol and 5% dextrose. To protect the injection from contamination of microorganisms, it may further comprise various antibiotics or antifungal reagent such as paraben, chlorobutanol, phenol, sorbic acid, thimerosal. In addition, in most cases, the injection may further comprise an isotonic reagent such as sugars or sodium chloride.

In case of transdermal preparations, it comprise ointments, creams, lotions, gels, topical solutions, paster, liniments and aerosols. The "transdermal preparations" means administering a pharmaceutical composition partially to skin and delivering effective amount of an active ingredient through the skin. The formulation of the above-mentioned is well described in Remington's Pharmaceutical Science, 15th Edition, 1975.

In case of nasal inhalers, a compound of the present invention may be delivered with a form of aerosol spray from pressure pack or spray by using proper propellants such as dichlorofluoromethane, trichlorofluoromethane, dichlorotetrafluoroethane, carbon dioxide or other proper gas. In case of pressure aerosols, dose may be determined by providing valve which delivers the measured amount of a compound. For example, a gelatin capsule and cartridge for inhaler or insufflator may be formulated to contain compound, and proper powder compound such as lactose or starch.

Other pharmaceutically acceptable carriers are well described in Remington's Pharmaceutical Sciences, 19th Edition, Mack Publishing Company, Easton, Pa., 1995.

Also, a pharmaceutical composition of the present invention may further comprise one or more buffers (e.g. saline or PBS), carbohydrates (e.g. glucose, mannose, sucrose or dextran), antioxidant, bacteriostat, chelating agent (e.g. EDTA or glutathione), adjuvant (e.g. aluminiumhydroxide), suspension agent, thickening agent and/or preservative.

Also, a pharmaceutical composition of the present invention may be formulated using a method well known in the art to provide quick, durable, delayed release of an active ingredient after administration.

Also, a pharmaceutical composition of the present invention may be administered together with a well known composition having effects on preventing and treating obesity, hyperlipidemia, hypercholesterolemia and diabetes.

As used herein, the "effective amount" refers to the amount effective in treating disease of a subject, and the "subject" refers to mammals, particularly, animals comprising human. The subject may be patient in need of treatment.

The panduratin derivative or the *Boesenbergia pandurata* extract of the present invention may be provided in the form of a food composition to prevent or relieve obesity, hyperlipidemia, hypercholesterolemia or diabetes. The food composition of the present invention encompasses all food types, including functional food, nutritional supplements, health food, food additives and animal feed, for humans or animals including livestock. The food composition may be prepared into various forms according to methods known in the related art.

For example, the health food may be prepared into the form of tea, juice or drink for drinking. Alternatively, the panduratin derivative or the *Boesenbergia pandurata* extract of the present invention may be formulated into granule, capsule or powder. In addition, the panduratin derivative or the *Boesenbergia pandurata* extract of the present invention may be formulated by mixing with other known active ingredients effective in preventing or relieving obesity, hyperlipidemia, hypercholesterolemia or diabetes.

Also, the functional food may be prepared by adding the panduratin derivative or the *Boesenbergia pandurata* extract of the present invention to beverages (including alcoholic beverages), fruits and processed foods thereof (e.g.: canned fruits, bottled fruits, jam, marmalade and the like), fishes, meats and processed foods thereof (e.g.: ham, sausages, corn beef), bread and noodles (e.g.: Japanese noodles, buckwheat noodles, ramen, spaghetti, macaroni and the like), juices, drinks, cookies, Korean taffy, dairy products (e.g.: butter, cheese and the like), eatable plant oils, margarine, plant proteins, retort foods, frozen foods, various seasonings (e.g.: soybean paste, soy sauce, sauce and the like).

Also, to use the panduratin derivative or the *Boesenbergia pandurata* extract of the present invention for food additives, it may be formulated into powder or concentrated solution.

Preferable amount of the panduratin derivative or the *Boesenbergia pandurata* extract in a food composition of the present invention may be 0.01 to 99.99 weight % and the rest may be an acceptable carrier for food compositions.

The obese-diabetic mouse (ob/ob mouse) is a leptin-deficient mutant mouse that eats excessively due to uncontrolled appetite. As a result, fat is overly accumulated in the body. A 3-month-old mouse weighs about 50 g, twice that of the normal mouse. It is the typical animal model of type 2 diabetes with higher blood glucose level than the normal mouse (*Exp. Clin. Endocrinol. Diabetes*, 109: 307-319, 2001). The obese-diabetic mouse is widely used in searching for preventive or therapeutic agents against obesity or diabetes or evaluating anti-obesity or anti-diabetic effects. The effect of the panduratin derivative and the *Boesenbergia pandurata* extract of the present invention was investigated using the obese-diabetic mouse model. As a result, the panduratin derivative and the *Boesenbergia pandurata* extract exhibited significant effect in the obese-diabetic mouse model, suggesting that they are effective in suppressing obesity and diabetes, especially type 2 diabetes. Therefore, the panduratin derivative or the *Boesenbergia pandurata* extract of the present invention is effective in diabetes, particularly type 2 diabetes.

Advantageous Effects

Accordingly, the present invention provides a novel use of a panduratin derivative or a *Boesenbergia pandurata* extract. A panduratin derivative or a *Boesenbergia pandurata* extract of the present invention shows excellent effects on a metabolic disease such as obesity, hyperlipidemia, hypercholesterolemia and diabetes by decreasing highly related causes of metabolic diseases such as on weight, body fat and lipid-content. Since a composition of the present invention is originated from natural materials, it can be used without side effect and provides novel method for preventing and treating/relieving a metabolic disease through body weight loss and body fat loss and the like.

MODE FOR INVENTION

The examples and experiments will now be described. The following examples and experiments are for illustrative purposes only and not intended to limit the scope of the present invention.

Example 1

Preparation of *Boesenbergia pandurata* Extract Including Panduratin

Dried *Boesenbergia pandurata* was pulverized using a mixer. The pulverized *Boesenbergia pandurata* sample (100 g) was added to ethanol (500 mL), and the mixture was stirred at 50 t for 30 minutes to perform extraction. The extracted sample was filtered through Whatman No. 2 filter paper, and the filtered extract was concentrated using a rotary vacuum concentrator to remove the solvent. Then, the resultant was lyophilized to remove moisture to obtain *Boesenbergia pandurata* extract.

Example 2

Isolation and Identification of Panduratin A

<2-1> Isolation of Panduratin A

The concentrated *Boesenbergia pandurata* extract obtained in Example 1 was mixed with ethyl acetate to extract ingredients soluble in ethyl acetate. The ethyl acetate was removed under reduced pressure to concentrate the ingredients soluble in ethyl acetate. Then, the concentrated ingredients were loaded onto a column filled with silica gel (6×15 cm) and eluted using a solvent system comprising hexane, chloroform, and ethyl acetate at a ratio of 15:5:1.5 (v/v/v). The collection obtained from the elution was divided into 6 fractions according to the eluting order, and each fraction was concentrated and dried. The third fraction (Fraction 3) among the 6 fractions was further separated by thin layer chromatography (TLC, silica gel 60F254, Merck) with a developing solvent of hexane, ethyl acetate, and methanol at a ratio of 18:2:1 (v/v/v). As a result, 3 fractions were collected according to the eluting order, and each fraction was concentrated and dried. The second among the 3 fractions (Fraction 32) was further separated by recycling high-performance liquid chromatography (recycling HPLC, column: W252, 20.0 mm ID×500 mm L). Two fractions were collected according to the eluting order, and each fraction was concentrated and dried. Finally, the second of the 2 fractions (Fraction 322) was concentrated and dried to isolate a pure, active ingredient.

<2-2> Identification of Panduratin A

In order to identify the active ingredient isolated in Example <2-1>, $^1$H-NMR spectrum and $^{13}$C-NMR spectrum were obtained respectively at 500 MHz and 125 MHz (solvent: CDCl$_3$). In order to identify the $^1$H-$^1$H and $^1$H-$^{13}$C relationships based on the $^{13}$C-NMR and $^1$H-NMR spectra, $^1$H-$^1$H COSY spectrum and $^1$H-$^{13}$C HSQC spectrum were obtained, and the signal of each carbon was identified using wavelengths from carbon resonance.

In addition, EI/MS measurement was made for mass analysis of the active ingredient. Since [M$^+$H$^+$] was observed in m/z 407 in the EI/MS spectrum, the molecular weight was measured at 406, and the molecular formula was $C_{26}H_{30}O_4$.

By comparing the results of $^1$H-NMR, $^{13}$C-NMR, $^1$H-$^1$H COSY, $^1$H-$^{13}$C HSQC and EI/MS spectra with the previous report (Woo, W. S. et al., *Phytochemistry*, 26: 1542-1543, 1987), it was identified that the active ingredient isolated in Example <2-1> was (2,6-dihydroxy-4-methoxyphenyl)[3-methyl-2-(3-methylbut-2-enyl)-5-phenylcyclohex-3-enyl]methanone, i.e. panduratin A represented by Chemical Formula 1.

<Chemical Formula>

Example 3

Isolation and Identification of Isopanduratin A

<3-1> Isolation of Isopanduratin A

The concentrated *Boesenbergia pandurata* extract obtained in Example 1 was mixed with ethyl acetate to extract ingredients soluble in ethyl acetate. The ethyl acetate was removed under reduced pressure to concentrate the ingredients soluble in ethyl acetate. Then, the concentrated ingredients were loaded onto a column filled with silica gel (6×15 cm) and eluted using a solvent system comprising hexane, chloroform, and ethyl acetate at a ratio of 15:5:1.5 (v/v/v). The collection obtained from the elution was divided into 6 fractions according to the eluting order, and each fraction was concentrated and dried. The fourth fraction (Fraction 4) among the 6 fractions was further separated by reversed phase-18 (Rp18, LiChropep, 2540 m) column chromatography using a solvent system comprising methanol and water at a ratio of 9:1 (v/v). The collection was divided into 2 fractions according to the eluting order. The second of the 2 fractions (Fraction 42) was concentrated and dried, and further separated by eluting using a solvent system comprising chloroform and methanol at a ratio of 10:0.2 (v/v). Then, the collection was divided into 2 fractions according to the eluting order, and each fraction was concentrated and dried. The second of the 2 fractions (Fraction 422) was further separated by eluting using a solvent system comprising hexane and ethyl acetate at a ratio of 10:3 (v/v). The collection obtained was divided into 2 fractions according to the eluting order, and each fraction was concentrated and dried. Finally, the second of the 2 fractions (Fraction 4222) was concentrated and dried to isolate a pure, active ingredient.

<3-2> Identification of Isopanduratin A

In order to identify the active ingredient isolated in Example <3-1>, $^1$H-NMR spectrum and $^{13}$C-NMR spectrum were obtained respectively at 500 MHz and 125 MHz (solvent: CDCl$_3$). In order to identify the $^1$H-$^1$H and $^1$H-$^{13}$C relationships based on the $^{13}$C-NMR and $^1$H-NMR spectra, $^1$H-$^1$H COSY spectrum and $^1$H-$^{13}$C HSQC spectrum were obtained, and the signal of each carbon was identified using wavelengths from carbon resonance.

In addition, EI/MS measurement was made for mass analysis of the active ingredient. Since [M$^+$H$^+$] was observed in m/z 407 in the EI/MS spectrum, the molecular weight was measured at 406, and the molecular formula was $C_{26}H_{30}O_4$.

By comparing the results of $^1$H-NMR, $^{13}$C-NMR, $^1$H-$^1$H COSY, $^1$H-$^{13}$C HSQC and EI/MS spectra with the previous report (Woo, W. S. et al., *Phytochemistry*, 26: 1542-1543, 1987), it was identified that the active ingredient isolated in Example <3-1> was (4,6-dihydroxy-2-methoxyphenyl)[3-methyl-2-(3-methylbut-2-enyl)-6-phenylcyclohex-3-enyl]methanone, i.e. isopanduratin A represented by Chemical Formula 2.

<Chemical Formula 2>

Example 4

Isolation and Identification of 4-hydroxypanduratin A

<4-1> Isolation of 4-hydroxypanduratin A

The concentrated *Boesenbergia pandurata* extract obtained in Example 1 was mixed with ethyl acetate to extract ingredients soluble in ethyl acetate. The ethyl acetate was removed under reduced pressure to concentrate the ingredients soluble in ethyl acetate. Then, the concentrated ingredients were loaded onto a column filled with silica gel (6×15 cm) and eluted using a solvent system comprising hexane, chloroform, and ethyl acetate at a ratio of 15:5:1.5 (v/v/v). The collection obtained from the elution was divided into 6 fractions according to the eluting order, and each fraction was concentrated and dried. The sixth fraction (Fraction 6) among the 6 fractions was further separated by eluting using a solvent system comprising methylene chloride and methanol at a ratio of 19:1 (v/v). The collection was divided into 3 fractions according to the eluting order. The second among the 3 fractions (Fraction 62) was further separated by eluting using a solvent system comprising chloroform and methanol at a ratio of 20:1 (v/v). Then, the collection was divided into 2 fractions according to the eluting order. Finally, the second of the 2 fractions (Fraction 622) was separated by recycling HPLC (column: W252, 20.0 mm ID×500 mm L) to isolate a pure, active ingredient.

<4-2> Identification of 4-hydroxypanduratin A

In order to identify the active ingredient isolated in Example <4-1>, $^1$H-NMR spectrum and $^{13}$C-NMR spectrum were obtained respectively at 500 MHz and 125 MHz (solvent: methanol). In order to identify the $^1$H-$^1$H and $^1$H-$^{13}$C relationships based on the $^{13}$C-NMR and $^1$H-NMR spectra, $^1$H-$^1$H COSY spectrum and $^1$H-$^{13}$C HSQC spectrum were obtained, and the signal of each carbon was identified using wavelengths from carbon resonance.

In addition, EI/MS measurement was made for mass analysis of the active ingredient. Since [M$^+$H$^+$] was observed in m/z 393 in the EI/MS spectrum, the molecular weight was measured at 392, and the molecular formula was $C_{25}H_{28}O_1$.

By comparing the results of $^1$H-NMR, $^{13}$C-NMR, $^1$H-$^1$H COSY, $^1$H-$^{13}$C HSQC and EI/MS spectra with the previous report (Woo, W. S. et al., *Phytochemistry*, 26: 1542-1543, 1987), it was identified that the active ingredient isolated in Example <4-1> was (2,4,6-trihydroxyphenyl[3-methyl-2-(3-methylbut-2-enyl)-6-phenylcyclohex-3-enyl]methanone, i.e. 4-hydroxypanduratin represented by Chemical Formula 3.

<Chemical Formula 3>

Example 5

Body Weight-Reducing Effect of Panduratin A in Mice in which Obesity is Induced with a High-Fat Diet Mice in which obesity is induced with a high-fat diet were selected as a model to investigate the obesity-relieving effect of panduratin A prepared in Example 2. 3-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 12 per each group. For the test group, panduratin A suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. Then, food intake and body weight of the mice were measured every week, for 8 weeks.

Figure 1:
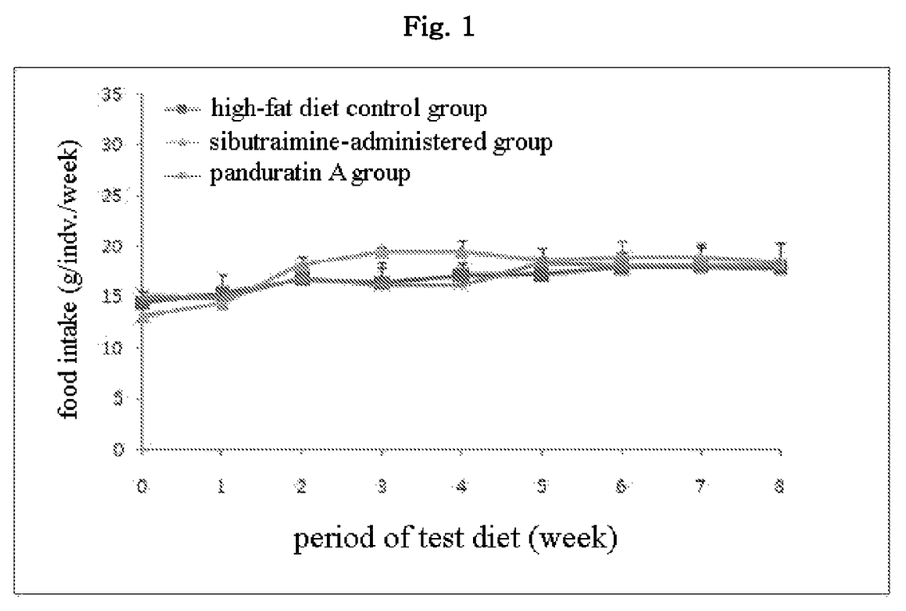
FIG. 1 shows a result of comparing food intake of a high-fat diet control group, a sibutramine-administered group, and a panduratin A-administered group.
Figure 2:
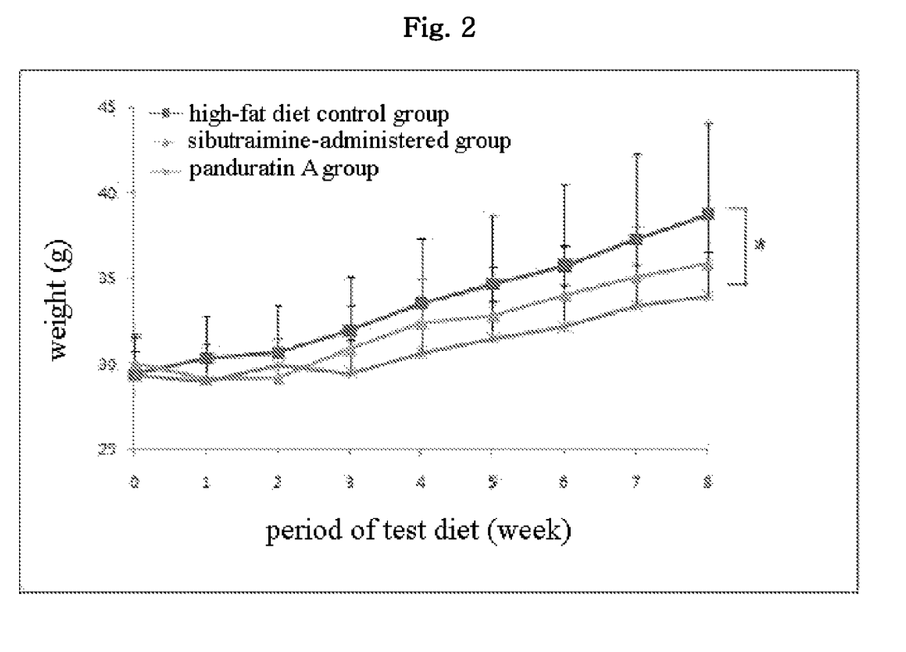
FIG. 2 shows a result of measuring change in body weight of mice in which obesity is induced with a high-fat diet after treatment with panduratin A.

As seen from FIG. 1, there was no difference between the test group and other groups in food intake. And, as seen from FIG. 2, the high-fat diet control group and the panduratin A group showed body weight increase of about 32% and 15%, respectively, after 8 weeks. The body weight increase of the panduratin A group was significantly lower than that of the high-fat diet control group (p<0.05). In contrast, the sibutramine-administered group showed body weight increase of about 20%. Thus, panduratin A exhibited better body weight-reducing effect than sibutramine, which is currently used as an anti-obesity drug. Accordingly, it was confirmed that panduratin A can effectively reduce body weight.

Example 6

Change of Total Blood Cholesterol Level, Triglyceride Level, Total Lipid Level and Leptin Level by Panduratin A Treatment in Mice in which Obesity is Induced with a High-Fat Diet 3-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 12 per each group. For the test group, panduratin A suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. After administration for 8 weeks, the mice were fasted for at least 12 hours. After cutting open the abdomen, blood was taken from the heart. The blood was centrifuged at 2,800 rpm at 4° C. for 30 minutes to separate the serum. The separated serum was stored at −70° C.

Total cholesterol level in the serum was determined by measuring absorbance at 500 nm using a standard enzyme assay kit. Serum triglyceride level was determined by measuring absorbance at 546 nm using a glycerol phosphate oxidase assay kit. Serum total lipid level was determined by measuring absorbance at 540 nm by the Frings method. Serum leptin level was determined by radioimmunoassay (RIA) using a mouse leptin RIA kit (Linco Research, Inc. USA).

Figure 3:
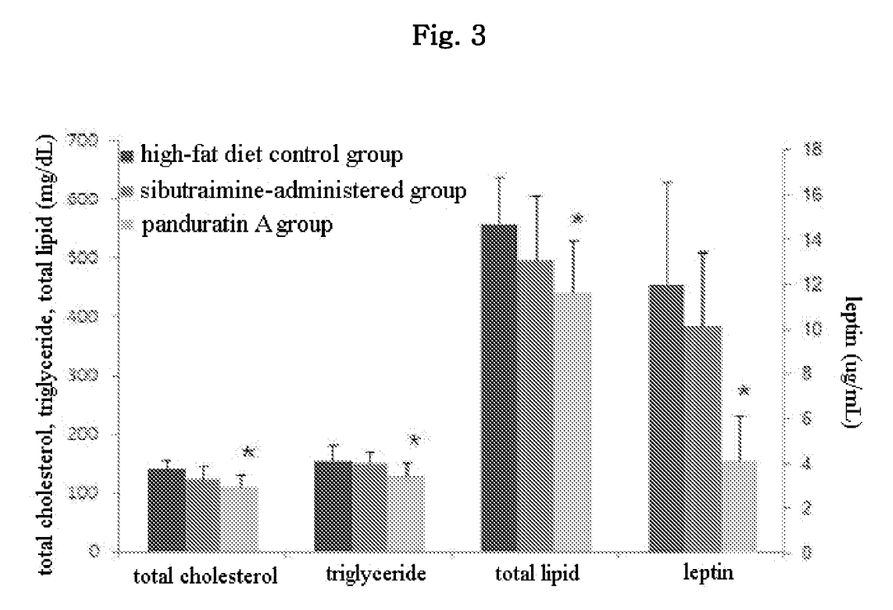
FIG. 3 shows a result of measuring total blood cholesterol level, triglyceride level, total lipid level and leptin level of mice in which obesity is induced with a high-fat diet after treatment with panduratin A.

As seen from FIG. 3, the total cholesterol level in the serum was 140.73±16.47 (mg/dL) for the control group, and 122.4±22.6 (mg/dL) for the sibutramine group. In contrast, the panduratin A group showed significantly lower total cholesterol level of 108.8±21.8 (mg/dL) (p<0.05). The serum triglyceride level was 154.36±27.02 (mg/dL) for the control group and 150.2±20.19 (mg/dL) for the sibutramine group. The panduratin A group showed significantly lower triglyceride level of 129±22.16 (mg/dL) (p<0.05). The total lipid level in the serum of the control group, the sibutramine group, and the panduratin A group was 555.18±80.86 (mg/dL), 493.2±111.9 (mg/dL), and 439.6±88 (mg/dL), respectively. The panduratin A group showed a decrease of 21% as compared to the control group (p<0.05). The serum leptin level was 12±4.6 (μg/mL) for the control group and 10.1±3.4 (μg/mL) for the sibutramine group. The panduratin A group showed remarkably decreased serum leptin level of 4.1±2 (μg/mL) (p<0.05). Accordingly, it was confirmed that panduratin A has a superior blood lipid-reducing effect.

Example 7

Change of Body Fat by Panduratin A Treatment in Mice in which Obesity is Induced with a High-Fat Diet 3-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 12 per each group. For the test group, panduratin A suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. After administration for 8 weeks, the mice were fasted for at least 12 hours. After cutting open the abdomen, perirenal fat and epididymal fat were taken out, washed with physiological saline, dried, and then weighed.

Figure 4:
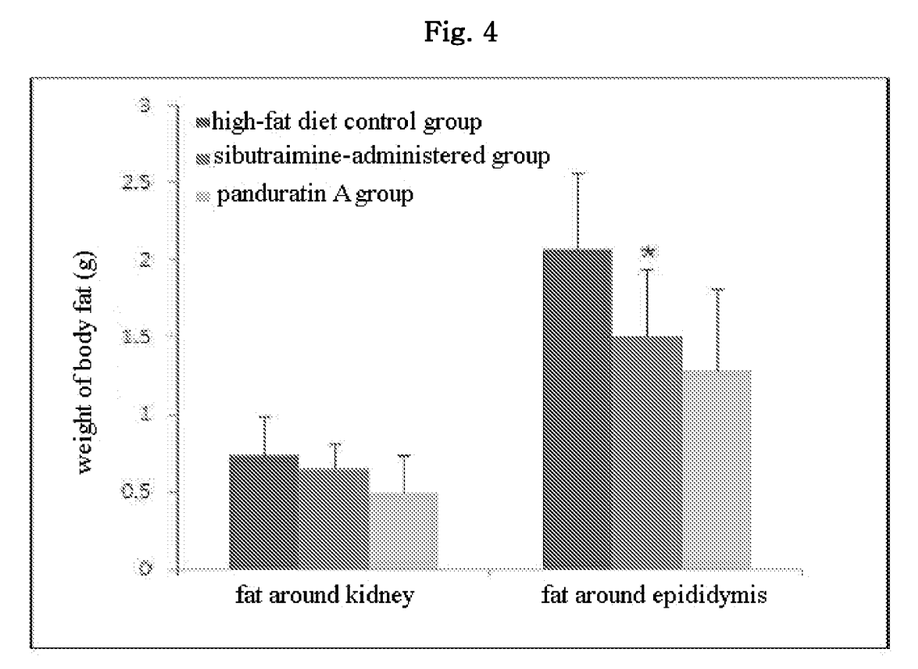
FIG. 4 shows a result of measuring change in body fat of mice in which obesity is induced with a high-fat diet after treatment with panduratin A.
Figure 5:
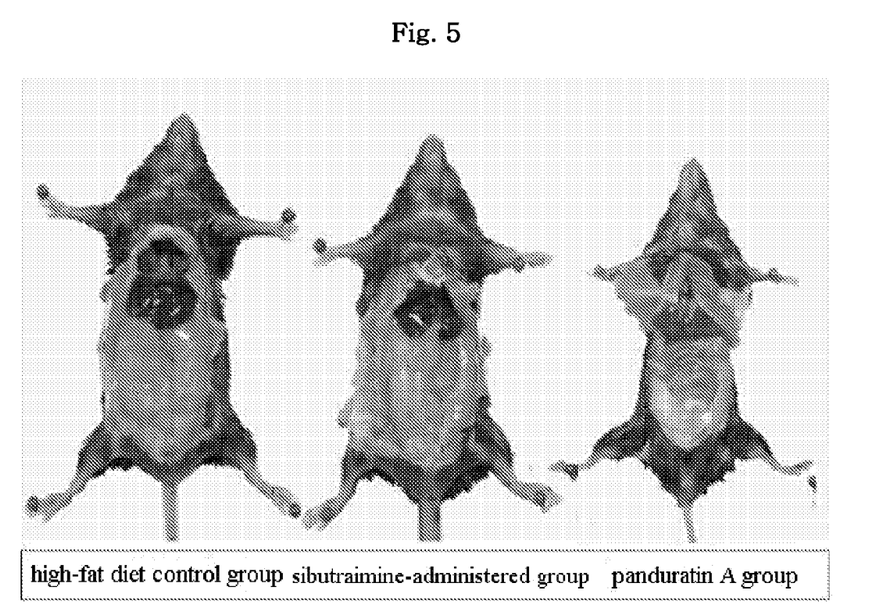
FIG. 5 shows a change in body shape of mice in which obesity is induced with a high-fat diet after treatment with panduratin A.

As seen from FIG. 5, the panduratin A group had significantly reduced abdominal fat as compared to the sibutramine group or the high-fat diet control group. And, as seen from FIG. 4, the panduratin A group showed significantly decreased weight of perirenal fat and epididymal fat as compared to the high-fat diet control group (p<0.05). Under the same condition, the test group showed more fat weight decrease than the sibutramine group. To conclude, it was confirmed that panduratin A has a superior body fat-reducing effect.

Example 8

Change of Size of Adipocytes by Panduratin A Treatment in Mice in which Obesity is Induced with a High-Fat Diet 3-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 12 per each group. For the test group, panduratin A suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. After administration for 8 weeks, the mice were fasted for at least 12 hours. After cutting open the abdomen, subcutaneous fat was quickly taken out and immobilized by immersing in 4% formaldehyde solution. After washing with water and dehydrating, paraffin blocks were prepared by treating the immobilized subcutaneous fat with paraffin solution, which were then sliced into 4 μm thickness, stained with hematoxylin and eosin, and observed under an optical microscope.

Figure 6:
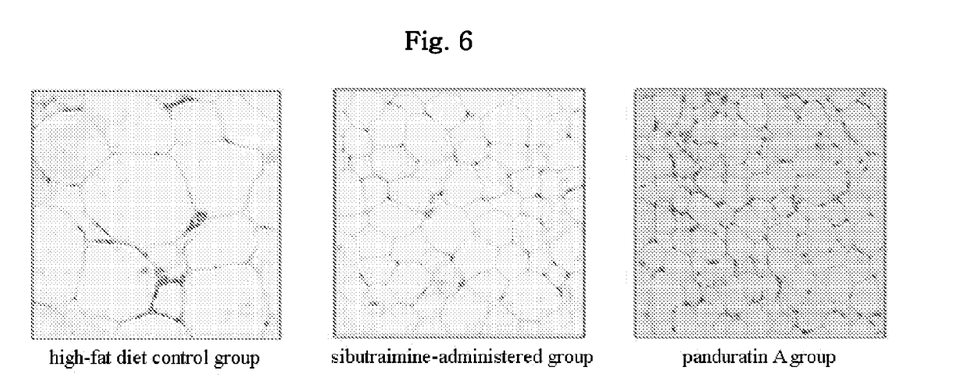
FIG. 6 shows change in adipocytes of mice in which obesity is induced with a high-fat diet after treatment with panduratin A.

As seen from FIG. 6, the size of adipocytes of the panduratin A group decreased significantly, almost comparable to that of the normal group, unlike the high-fat diet control group. Under the same condition, the panduratin A group showed more reduction of adipocytes size than the sibutramine group. Accordingly, it was confirmed that panduratin A has a superior effect of reducing adipocyte size.

Example 9

Morphological Change of Subcutaneous Tissue by Panduratin A Treatment in Mice in which Obesity is Induced with a High-Fat Diet 3-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 12 per each group. For the test group, panduratin A suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. After administration for 8 weeks, the mice were fasted for at least 12 hours. After cutting open the abdomen, subcutaneous fat was quickly taken out and immobilized by immersing in 4% formaldehyde solution. After washing with water and dehydrating, paraffin blocks were prepared by treating the immobilized subcutaneous fat with paraffin solution, which were then sliced into 4 μm thickness, stained with hematoxylin and eosin, and observed under an optical microscope.

Figure 7:
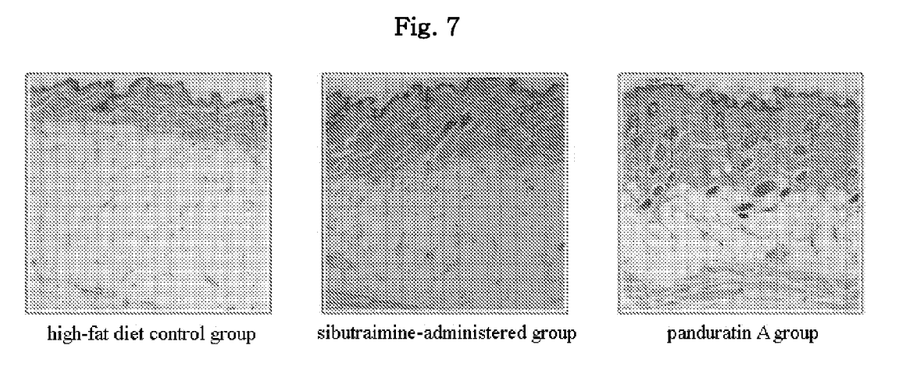
FIG. 7 shows morphological change of subcutaneous tissue of mice in which obesity is induced with a high-fat diet after treatment with panduratin A.

As seen from FIG. 7, the panduratin A group showed significantly reduced subcutaneous fat layer as compared to the high-fat diet control group. Under the same condition, the panduratin A group showed better effect of reducing the subcutaneous fat layer than the sibutramine group. Accordingly, it was confirmed that panduratin A has a superior effect of reducing the subcutaneous fat layer.

Example 10

Effect of Isopanduratin A on Body Weight and Body Fat Reduction In Mice in which Obesity is Induced with a High-Fat Diet The effect of isopanduratin A prepared in Example 3 on body weight and body fat decrease was investigated in the same manner as in Examples 5 and 6. After administration for 8 weeks, there was no difference between the test group and other groups in food intake. The high-fat diet control group and the isopanduratin A group showed body weight increase of about 32% and 17%, respectively, after 8 weeks. The body weight increase of the isopanduratin A group was significantly lower than that of the high-fat diet control group ($p<0.05$). Furthermore, the isopanduratin A group showed decrease of perirenal fat and epididymal fat weight by 25% and 32%, respectively, as compared to the high-fat diet control group ($p<0.05$). To conclude, it was confirmed that isopanduratin A has a superior effect of reducing body weight and body fat.

Example 11

Effect of 4-hydroxypanduratin A on Body Weight and Body Fat Reduction in Mice in which Obesity is Induced with a High-Fat Diet The effect of 4-hydroxypanduratin A prepared in Example 4 on body weight and body fat decrease was investigated in the same manner as in Examples 5 and 6. After administration for 8 weeks, there was no difference between the 4-hydroxypanduratin-administered test group and other groups in food intake. The high-fat diet control group and the 4-hydroxypanduratin A group showed body weight increase of about 32% and 13%, respectively, after 8 weeks. The body weight increase of the 4-hydroxypanduratin A group was significantly lower than that of the high-fat diet control group ($p<0.05$). Furthermore, the 4-hydroxypanduratin A group showed decrease of perirenal fat and epididymal fat weight by 33% and 46%, respectively, as compared to the high-fat diet control group ($p<0.05$) To conclude, it was confirmed that 4-hydroxypanduratin A has a superior effect of reducing body weight and body fat.

Example 12

Body Weight-Reducing Effect of *Boesenbergia pandurata* Extract in Mice in which Obesity is Induced with a High-Fat Diet Mice in which obesity is induced with a high-fat diet were selected as a model to investigate the obesity-relieving effect of the *Boesenbergia pandurata* extract prepared in Example 1. 4-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 8 per each group. For the test group, *Boesenbergia pandurata* extract suspended in 0.25% carboxymethyl cellulose was administered once a day at regular hours for 8 weeks, with an administration dose of 200 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. Then, food intake and body weight of the mice were measured every week, for 8 weeks.

Figure 8:
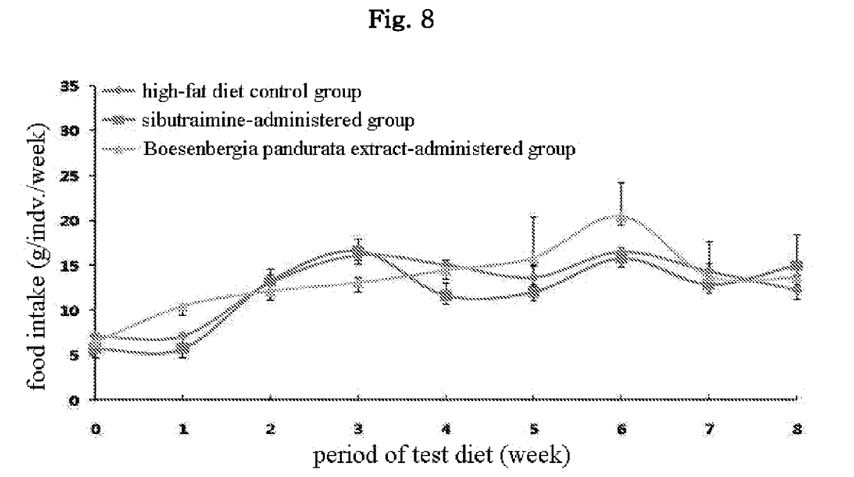
FIG. 8 shows a result of measuring comparing food intake of a high-fat diet control group, a sibutramine-administered group, and a *Boesenbergia pandurata* extract-administered group.
Figure 9:
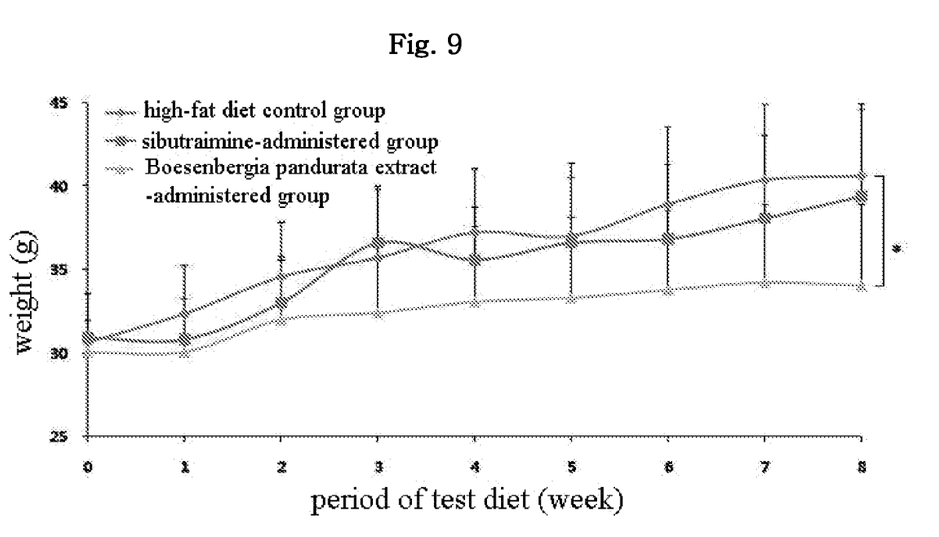
FIG. 9 shows a result of measuring change in body weight of mice in which obesity is induced with a high-fat diet after treatment with *Boesenbergia pandurata* extract.

As seen from FIG. 8, there was no significant difference between the test group and other groups in food intake. The high-fat diet control group and the *Boesenbergia pandurata* extract group showed body weight increase of about 33% and 13%, respectively, after 8 weeks (see FIG. 9). The body weight increase of the *Boesenbergia pandurata* extract group was significantly lower than that of the high-fat diet control group ($p<0.05$). In contrast, the sibutramine-administered group showed body weight increase of about 27%. Thus, *Boesenbergia pandurata* extract exhibited better body weight-reducing effect than sibutramine, which is currently used as an anti-obesity drug. Accordingly, it was confirmed that *Boesenbergia pandurata* extract can effectively reduce body weight.

Example 13

Change of Body Fat by *Boesenbergia pandurata* Extract Treatment in Mice in which Obesity is Induced with a High-Fat Diet 4-week-old C57BL/6 mice were accustomed for a week, and a high-fat diet (Product # D12492, Research Diet Inc., New Brunswick, N.J., USA) was provided for 6 weeks to induce obesity. Then, the mice were randomly divided into 3 groups, 8 per each group. For the test group, *Boesenbergia pandurata* extract suspended in 0.25% carboxymethyl cellulose was administered once a day at regular hours for 8 weeks, with an administration dose of 50 mg/kg body weight. For comparison, 0.25% carboxymethyl cellulose only (control) of the same amount as that for the test group or sibutramine suspended in 0.25% carboxymethyl cellulose (5 mg/kg body weight) was orally administered. After administration for 8 weeks, the mice were fasted for at least 12 hours. After cutting open the abdomen, perirenal fat, epididymal fat, and subcutaneous fat from the back were taken out, washed with physiological saline, dried, and then weighed.

Figure 10:
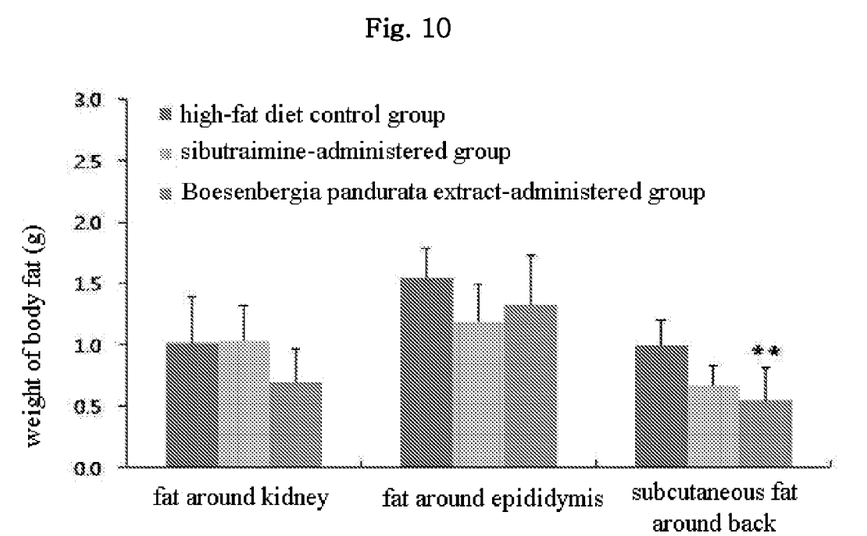
FIG. 10 shows a result of measuring change in body fat of mice in which obesity is induced with a high-fat diet after treatment with *Boesenbergia pandurata* extract.
Figure 11:
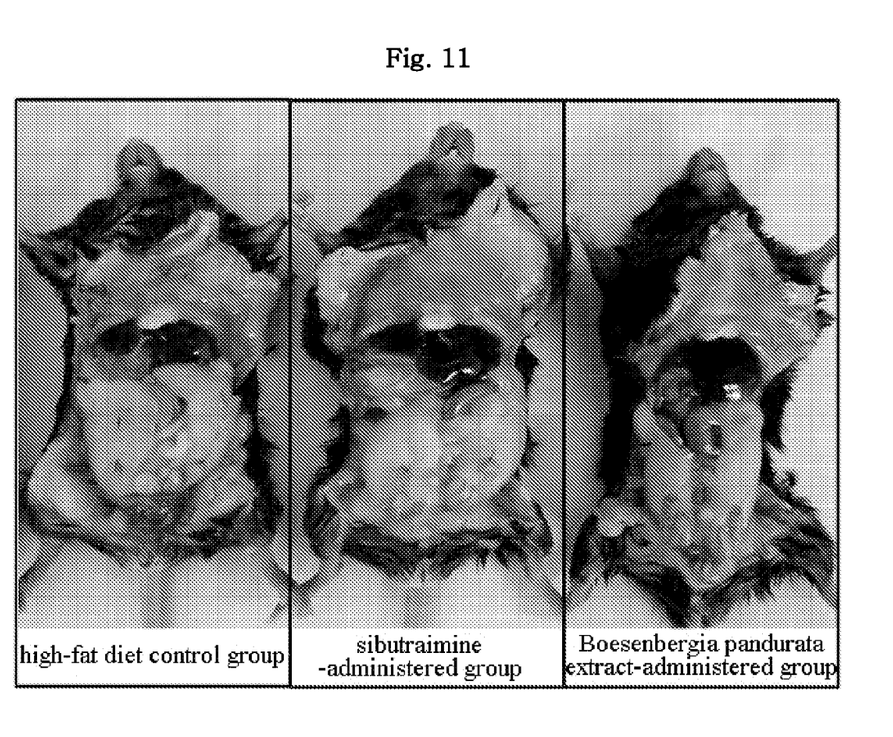
FIG. 11 shows a change in body shape of mice in which obesity is induced with a high-fat diet after treatment with *Boesenbergia pandurata* extract.

As seen from FIG. 11, the *Boesenbergia pandurata* extract group had significantly reduced abdominal fat as compared to the sibutramine group or the high-fat diet control group. And, as seen from FIG. 10, the *Boesenbergia pandurata* extract group showed significantly decreased weight of perirenal fat and epididymal fat as compared to the high-fat diet control group ($p<0.01$). Under the same condition, the test group showed more fat weight decrease than the sibutramine group. To conclude, it was confirmed that *Boesenbergia pandurata* extract has a superior body fat-reducing effect.

Example 14

Effect of Panduratin A on Activation (Phosphorylation) of AMPK and Deactivation (Phosphorylation) of its Substrate ACC in Metabolic Cells (Liver Cells)

Figure 12:
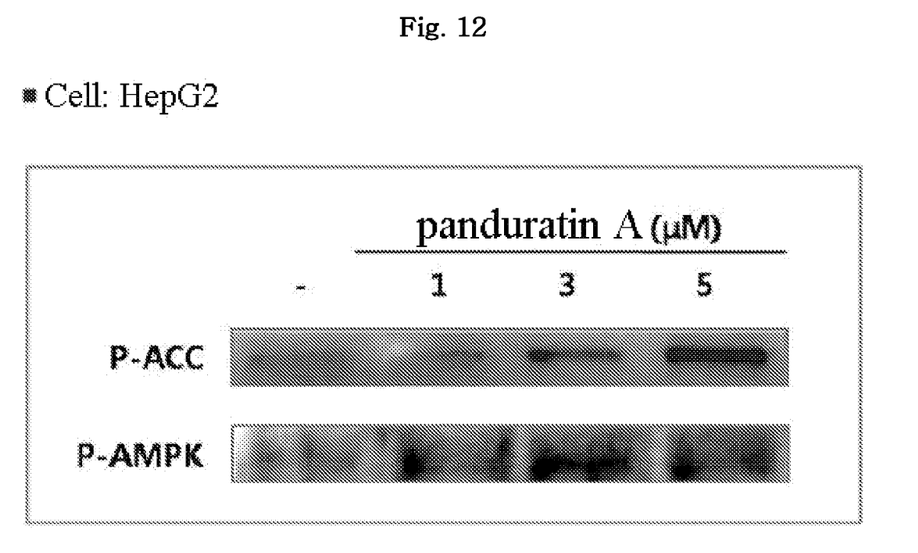
FIG. 12 shows a result of measuring activation of the energy-metabolizing protein AMPK in liver cells and inactivation of its substrate, the fat-producing protein ACC.

Activation of the AMPK protein and deactivation of the ACC protein by panduratin A prepared in Example 2 in liver cells were tested using HepG2 liver cells (ATCC HB-8065). The HepG2 cells were cultured in Dulbecco's modified Eagle's high-glucose medium (DMEM) containing 10% fetal bovine serum (FBS). After starving the HepG2 cells in serum-free DMEM for 3 hours, the cells were treated with panduratin A. 30 minutes later, proteins were acquired and subjected to western blotting. As seen from FIG. 12, the treatment with panduratin A resulted in increase of activated (phosphorylated) AMPK (p-AMPK), which reduces fat production and promotes energy consumption, and increase of deactivated (phosphorylated) ACC (p-ACC), which plays an important role in fat production. Accordingly, it was confirmed that treatment with panduratin A facilitates energy metabolism in liver cells, providing anti-obesity effect of inhibiting fat production and increasing energy consumption.

Example 15

Effect of Panduratin A on Activation (Phosphorylation) of AMPK and Deactivation (Phosphorylation) of its Substrate ACC in Metabolic Cells (Muscle Cells)

Figure 13:
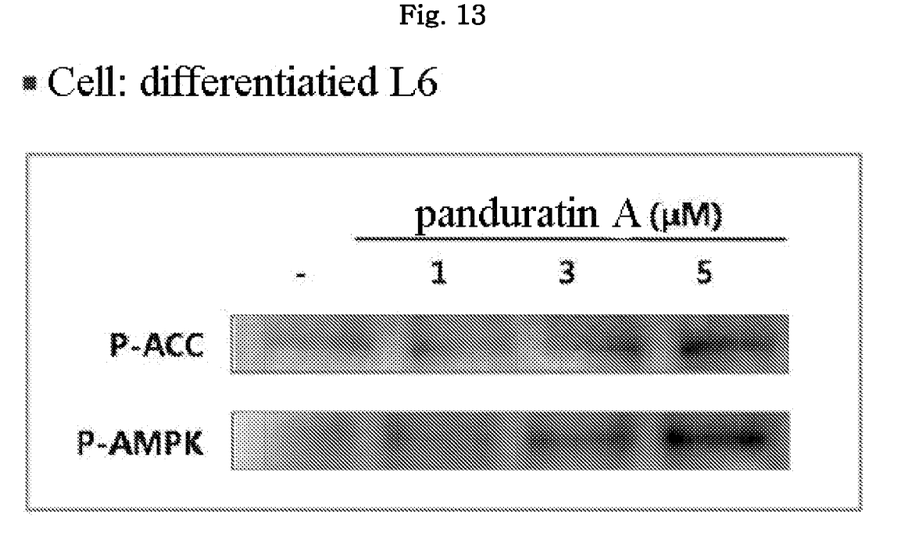
FIG. 13 shows a result of measuring activation of AMPK in muscle cells and inactivation of its substrate, ACC.

Activation of the AMPK protein and deactivation of the ACC protein by panduratin A prepared in Example 2 in muscle cells were tested using L6 muscle cells (ATCC CRL-1458). The L6 cells were cultured in DMEM containing 10% FBS. In order to differentiate the L6 muscle cells into muscle fibers, the cells were cultured while changing the medium with DMEM containing 2% horse serum every two days. On days 4-8 when the differentiation of the L6 cells was observed under a microscope, the L6 cells were starved in serum-free DMEM for 3 hours and were treated with panduratin A. 30 minutes later, proteins were acquired and subjected to western blotting. As seen from FIG. 13, the treatment with panduratin A resulted in increase of activated p-AMPK and increase of deactivated p-ACC. Accordingly, it was confirmed that treatment with panduratin A facilitates energy metabolism in L6 cells, providing anti-obesity effect of inhibiting fat production and increasing energy consumption.

Example 16

Figure 14:
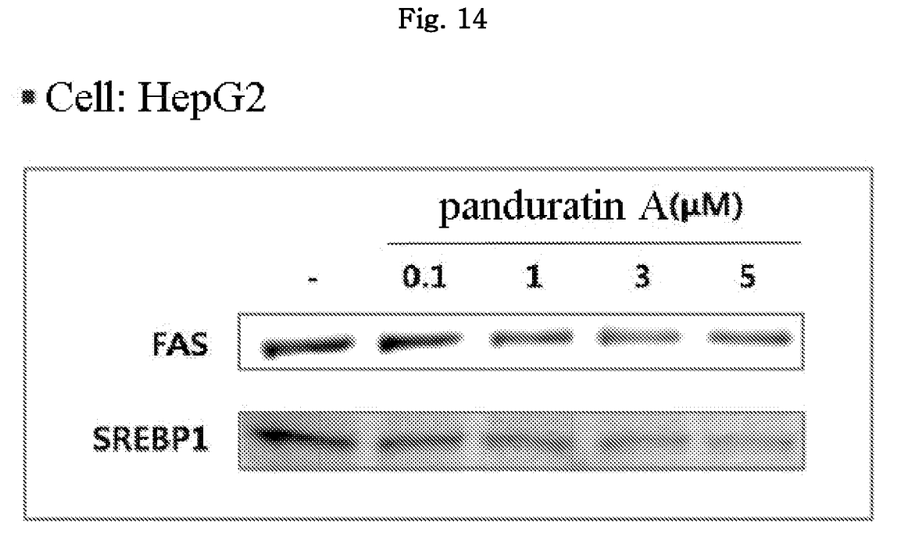
FIG. 14 shows a result of measuring decrease of the fat-producing protein transcription factor SREBP1 and the fat-producing fatty acid synthase (FAS) in liver cells.

Decrease of Fat-Producing Protein Transcription Factor and Expression of Fat-Producing Protein by Panduratin A Treatment in HepG2 Liver Cells Decrease in expression of fat-producing proteins by panduratin A prepared in Example 2 in liver cells were tested using HepG2 liver cells (ATCC HB-8065). The HepG2 cells were cultured in DMEM containing 10% FBS. After treating the cells with panduratin A for 24 hours in the same medium, western blotting was performed. As seen from FIG. 14, the treatment with panduratin A resulted in decreased expression of the fat production-related transcription factor SREBP1 and the fat production-related enzyme FAS. Accordingly, it was confirmed that treatment with panduratin A inhibits signal transduction in fat production pathway in HepG2 liver cells, thus inhibiting fat production.

Example of Preparation 1

Preparation of Granule

The panduratin derivative of the present invention or a salt thereof (10 mg) was mixed with lactose (700 mg), cornstarch (274 mg) and low-viscosity hydroxypropyl cellulose (16 mg), and prepared into granule according to a commonly employed method.

Example of Preparation 2

Preparation of Powder

The panduratin derivative of the present invention or a salt thereof (10 mg) was mixed with lactose (79 mg), cornstarch (10 mg) and magnesium stearate (1 mg), filled in an airtight pouch, and prepared into powder according to a commonly employed method.

Example of Preparation 3

Preparation of Tablet

The panduratin derivative of the present invention or a salt thereof (10 mg) was mixed with lactose (90 mg), microcrystalline cellulose (30 mg), magnesium stearate (5 mg) and sodium carboxymethyl cellulose (15 mg). The resulting mixture was prepared into tablet through direct compression.

Example of Preparation 4

Preparation of Injection

The panduratin derivative of the present invention or a salt thereof (100 mg) was mixed with saturated fatty acid glyceride (1000 ml) to prepare injection that can be administered via intravenous injection.

The injection may be intravenously injected at a rate of 1 mL/min.

Hereafter, the examples of preparation for food compositions are described in detail.

Example of Preparation 5

Preparation of Flour Food

The panduratin derivative of the present invention or a salt thereof (0.1-10.0 parts by weight) was added to flour. The resulting mixture was prepared into bread, cake, cookie, cracker or noodle according to a commonly employed method.

Example of Preparation 6

Preparation of Soup and Gravy

The panduratin derivative of the present invention or a salt thereof (0.1-1.0 part by weight) was added to soup or gravy, and prepared into soup or gravy for processed meat or noodle products according to a commonly employed method.

Example of Preparation 7

Preparation of Ground Beef

The panduratin derivative of the present invention or a salt thereof (10 parts by weight) was added to ground beef, and prepared into ground beef for health improvement according to a commonly employed method.

Example of Preparation 8

Preparation of Dairy Products

The panduratin derivative of the present invention or a salt thereof (0.1-1.0 part by weight) was added to milk, and was prepared into various dairy products such as butter and ice cream according to a commonly employed method.

Example of Preparation 9

Preparation of Health Food

For a daily dose, the panduratin derivative of the present invention or a salt thereof (100 mg) was mixed with ginseng extract (100 mg), green tea extract (100 mg), vitamin C (100 mg), vitamin E powder (120 mg), ferrous lactate (2 mg), zinc oxide (2 mg), nicotinamide (20 mg), vitamin A (5 mg), vitamin B1 (2 mg), vitamin B2 (2 mg), cornstarch (200 mg) and magnesium stearate (20 mg).

Example of Preparation 10

Preparation of Health Drink

The panduratin derivative of the present invention or a salt thereof was homogeneously mixed with high-fructose corn syrup (0.5%), oligosaccharide (2%), sugar (2%), table salt (0.5%) and water (75%), sterilized instantly, and filled in a glass bottle or a plastic bottle.

Example of Preparation 11

Preparation of Vegetable Juice

The panduratin derivative of the present invention or a salt thereof (5 g) was added to tomato or carrot juice (1,000 mL).

Example of Preparation 12

Preparation of Fruit Juice

The panduratin derivative of the present invention or a salt thereof (1 g) was added to apple or grape juice (1,000 mL).

INDUSTRIAL APPLICABILITY

As can be seen foregoing, the present invention provides a novel use of a panduratin derivative or a *Boesenbergia pandurata* extract. A panduratin derivative or a *Boesenbergia pandurata* extract of the present invention shows excellent effects on a metabolic disease such as obesity, hyperlipidemia, hypercholesterolemia and diabetes by decreasing highly related causes of metabolic diseases such as on weight, body fat and lipid-content. Since a composition of the present invention is originated from natural materials, it can be used without side effect and provides novel method for preventing and treating/relieving a metabolic disease through body weight loss and body fat loss and the like.

The invention claimed is:
1. A method for relieving and/or treating a metabolic disease selected from a group consisting of obesity, hyperlipidemia, and hypercholesterolemia, comprising a step of administering to a subject in need thereof an effective amount of a panduratin derivative selected from the group consisting of the compounds of Chemical Formula 1 to, 2 or 3, or salts thereof.

<Chemical Formula 1>

<Chemical Formula 2>

<Chemical Formula 3>

2. The method of claim 1, wherein the panduratin derivative is extracted from *Boesenbergia pandurata*.

* * * * *